United States Patent

Zeiher et al.

[11] Patent Number: 6,017,459
[45] Date of Patent: Jan. 25, 2000

[54] APPARATUS AND METHOD FOR THE MONITORING OF MEMBRANE DEPOSITION

[75] Inventors: E. H. Kelle Zeiher, Naperville; Brian F. Post, Lombard; William F. McCoy; Timothy L. Chaffin, both of Naperville, all of Ill.

[73] Assignee: Nalco Chemical Company, Naperville, Ill.

[21] Appl. No.: 08/027,872

[22] Filed: Mar. 8, 1993

[51] Int. Cl.[7] .......................... B01D 61/02; B01D 61/08; B01D 65/08

[52] U.S. Cl. ............... 210/650; 210/85; 210/94; 210/95; 210/96.2; 210/321.6; 210/323.1; 210/340; 210/652

[58] Field of Search ............... 55/270; 210/650, 210/651, 652, 254, 641, 340, 321.6, 94, 85, 96.2, 323.1, 95

[56] References Cited

U.S. PATENT DOCUMENTS 3,400,575  9/1968  Madden .............................. 210/94 X
4,389,879  6/1983  Bach et al. .......................... 73/61 R

FOREIGN PATENT DOCUMENTS 0109406  8/1980  Japan ................................. 210/641

*Primary Examiner*—John Kim
*Attorney, Agent, or Firm*—Thomas M. Breininger

[57] ABSTRACT

An in-line apparatus for monitoring membrane deposition is provided having an exterior body that defines an interior compartment for receiving a fluid stream. A coupon rack is positioned in the interior compartment and suspends at least one coupon holder. The coupon holder holds at least one membrane for collection of deposition present within a filtration system. The apparatus allows examination of membrane surface deposition without sacrificing a membrane element and also provides timely diagnostic information on a filtration system. The present invention also provides a method of monitoring membrane deposition as well as a filtration system incorporating an in-line apparatus for monitoring membrane deposition.

17 Claims, 3 Drawing Sheets

APPARATUS AND METHOD FOR THE MONITORING OF MEMBRANE DEPOSITION

BACKGROUND OF THE INVENTION

The present invention relates generally to the monitoring of filtration systems. More specifically, the present invention relates to the monitoring of reverse osmosis systems.

A vast array of businesses depend on filtration technology. Food and beverage industries, especially the beer and wine industry, utilize filtration systems everyday. Likewise, filtration systems are vital in the chemical processing, paper and refining industries. Among other things, filtering liquids is used to accomplish one or more of the following: water purification, concentration, purification of product solution or suspension, and removal of outside contaminants (sterilization).

The fine filtration of liquids is commonly referred to as membrane technology. Membrane processing is subdivided into three technologies: microfiltration, ultrafiltration and reverse osmosis. These technologies are used to separate suspended or dissolved materials from a solvent in applications ranging from contaminant removal for water purification to solute concentration in water treatment or processing applications. Cartwright, *An Overview of Fine Filtration Technology*, Pharmaceutical and Cosmetic Equipment, p. 39 (March, 1985)

Microfiltration involves removal of particulate material ranging in size from 0.1 to 10.0 microns. Ultrafiltration separates materials in the 0.001 to 0.1 micron range, whereas reverse osmosis is used for separations involving materials less than 0.001 micron in size. Microfiltration is primarily used for removal of suspended or colloidal materials; ultrafiltration and reverse osmosis are used for the separation of dissolved material (solute). Id.

Since many industries require high purity water, more and more industrial plants are installing reverse osmosis systems. A significant operating cost factor of a reverse osmosis systems is the cost of the membranes themselves. If properly maintained, membranes can last for years before replacement becomes necessary. However, deposition of material on membrane surfaces may result in increased energy consumption, or membrane failure which can ultimately cause an unscheduled shutdown and significant replacement costs. Accordingly, an utmost concern for plants using a reverse osmosis system is a proper monitoring program.

Membranes are susceptible to a loss of performance as a result of accumulation of small particles, colloids, oil, microorganisms, and precipitated salts on their surfaces. Some of these deposits cause catastrophic membrane failure in a short period of time, while others affect membrane performance over longer periods of time. These deposits are known as scaling and fouling, or collectively as membrane deposition.

Premature failure of reverse osmosis membrane elements due to identified or unidentified membrane fouling substances costs thousands to millions of dollars each year. Membrane fouling has been cited as the single largest cause, if not the only cause, of permeate flux decline at normal operating pressures and temperatures in brackish water systems. Fouling, as used in this context, refers to the accumulation of a substance or substances on or in the membrane. Such fouling causes a reduction in water transfer per unit area of membrane (flux). Paul et al, *Reverse Osmosis, Membrane Fouling—The Final Frontier?*, Ultrapure Water, p. 25 (April, 1990).

In addition to membrane fouling, other sources are known that lead to membrane destruction. For instance, as stated above, scaling can ultimately lead to the destruction of a reverse osmosis membrane. Scaling refers to a coating which forms on the membrane due to the precipitation or crystallization of salt compounds or solids.

Typical steps taken to prevent scaling include lowering the pH of the waters to reduce scaling potential, and feeding antiscalant treatments to ensure any scale that may form will remain in a dispersed state. In addition, extensive pre-treatment systems are frequently used to remove particulate matter (media and cartridge filters), iron (green sand filters), and other potential foulants. Zeiher et al, *Microbial Control, Biofouling of Reverse Osmosis Systems: Three Case Studies*, Ultrapure Water, p. 50 (October, 1991).

A variety of chemical and mechanical pre-treatments have been utilized in an attempt to control fouling. Treatments relating to the prevention of film formation fall into two main categories: (1) removal of fouling bacteria from the feedwater, and (2) metabolic inactivation by chemical means.

Complete removal of fouling from the feedwater can be technically problematic and economically unfeasible. One method often used is filtration of the feedwater. Due to the small size of most bacteria (<1 micron), pore sizes must be very small. This frequently results in rapid plugging of the filter by bacteria and colloids, forcing continual filter replacement.

Chemical addition may be the most effective method of feedwater pre-treatment. The application of the correct dosage at the correct frequency is essential in order to maintain a continuous active biocide residual on the membrane surface. Disinfection of the feedwater is most commonly achieved by the addition of chlorine or other oxidants. However, since composite membranes are degraded by oxidants, the oxidants must be removed before contacting the membrane. This, in turn, leaves the membrane surface vulnerable to microbial attack.

Moreover, another mechanical treatment method is ultraviolet sterilization. Although such ultraviolet sterilization can be effective, it does not provide an active residual, thereby permitting rapid regrowth of surviving bacteria. Accordingly, reverse osmosis systems are not infallible, and even the most extensively pre-treated water can cause fouling.

In an effort to prevent poor reverse osmosis performance, unscheduled down time, and the premature (and expensive) replacement of membrane elements, plants strive to set up an effective monitoring program. Probably the most common detection scheme relies on periodic monitoring of particular system parameters. To properly assess the performance of an entire bank of membrane elements, experts suggest that one must compare the current system performance to its start-up performance. In doing so, the three most useful performance parameters to track each day and evaluate carefully are: percent salt rejection, normalized permeate flow rate, and membrane bank differential pressure. These three performance parameters, in conjunction with the feedrate flow, approximate the extent of fouling, scaling, and membrane degregation—the three major causes of premature membrane element failure. Bukay, *Membranes, The Basis of Monitoring Reverse Osmosis—Part* 1, Ultrapure Water, pp. 58–59 (October, 1992).

On the other hand, while these parameters indicate the existence of a potential problem, they cannot provide accurate information regarding the source of the problem. For instance, when the system experiences a permeate flow loss, the technician is not able to determine whether fouling, scaling or some other source has caused the permeate flow loss. Moreover, periodic monitoring of these parameters only gives information about planktonic (suspended) organisms. Sessile (attached) organisms in water systems are of greater concern and often out number the planktonic counts by several orders of magnitude.

Other common detection schemes also do not provide effective results. Another detection scheme relies on scrapings taken from the housing during membrane cleaning and/or replacement. This technique often provides information too late, resulting in the need for membrane replacement. Moreover, often times the entire system must be shut down until the problem is identified, resulting in increased down time costs.

The other common detection scheme relies on destructive analysis. As the name implies, this technique requires the destruction of the membrane to allow for membranae surface micro-biological analysis. Naturally, this destructive technique is costly because the membranes cannot be returned to service. Resorting to these last two detection schemes can result in a loss of thousands of dollars in down time and membrane replacement costs.

Accordingly, while current monitoring programs facilitate the detection of membrane deposition, they fail to provide an accurate and early detection means. In fact, no published method for non-destructive observation of membrane surface fouling exists in the field. One expert has stated the following with respect to current monitoring programs:

Monitoring RO systems for fouling potential is a standard operating procedure at most facilities. That's the good news! The bad news is that there aren't any good monitoring methods that accurately predict either colloquial or biological fouling . . . It is obvious . . . that much more research is needed.

Paul et al, *Reverse Osmosis, Membrane Fouling—The Final Frontier?*, Ultrapure Water, pp. 30 & 33 (April, 1990).

SUMMARY OF THE INVENTION

The present invention provides an in-line apparatus for the monitoring of membrane deposition. The apparatus provides a monitoring means to accurately detect deposition on membranes while the system is operating.

The apparatus of the present invention simulates the membrane element used in a filtration system. Preferably, the apparatus has an exterior body defining an interior compartment for receiving a fluid stream, a coupon rack positioned in the interior compartment, and a coupon holder suspended in the coupon rack. The coupon holder holds a membrane for collecting deposition passing through the filtration system.

In an embodiment, the apparatus has support means for suspending a plurality of coupon holders. Preferably, the coupon racks are suspended in such a manner that the membrane is parallel to the direction of fluid flow through the interior compartment.

In another embodiment, the exterior body of the apparatus includes a window for observation of film formation.

The present invention also provides a method for detecting membrane deposition. First, a fluid stream is passed through an exterior body containing an interior compartment for receiving the fluid stream, and a coupon holder suspended in a coupon rack, wherein the coupon holder holds a membrane for collecting fouling present within a filtration system. Next, the membrane is removed from the interior compartment. Then, standard tests are conducted on the membrane coupon.

In an embodiment, the method for detecting membrane deposition further includes the step of staining the membrane prior to conducting standard tests on the membrane coupon.

An advantage of the present invention is that it provides an in-line monitoring apparatus that significantly decreases the down time of the filtration system.

Still further, the present invention provides an in-line monitoring apparatus that facilitates quick and accurate analysis of problems in the filtration system, thereby allowing more frequent testing.

A further advantage of the present invention is that it provides an in-line monitoring apparatus that can be used to compare the utility of various treatments, such as chemical and mechanical treatments.

Additional features and advantages of the present invention are described in, and will be apparent from, the detailed description of the presently preferred embodiments as well as the drawings.

DETAILED DESCRIPTION OF THE PRESENTLY PREFERRED EMBODIMENTS

The present invention provides an apparatus for monitoring membrane deposition that can be placed in-line while a filtration system is running. The apparatus provides an examination and evaluation of membrane surface deposition without sacrificing a membrane element and provides timely diagnostic information on the system.

Figure 1:
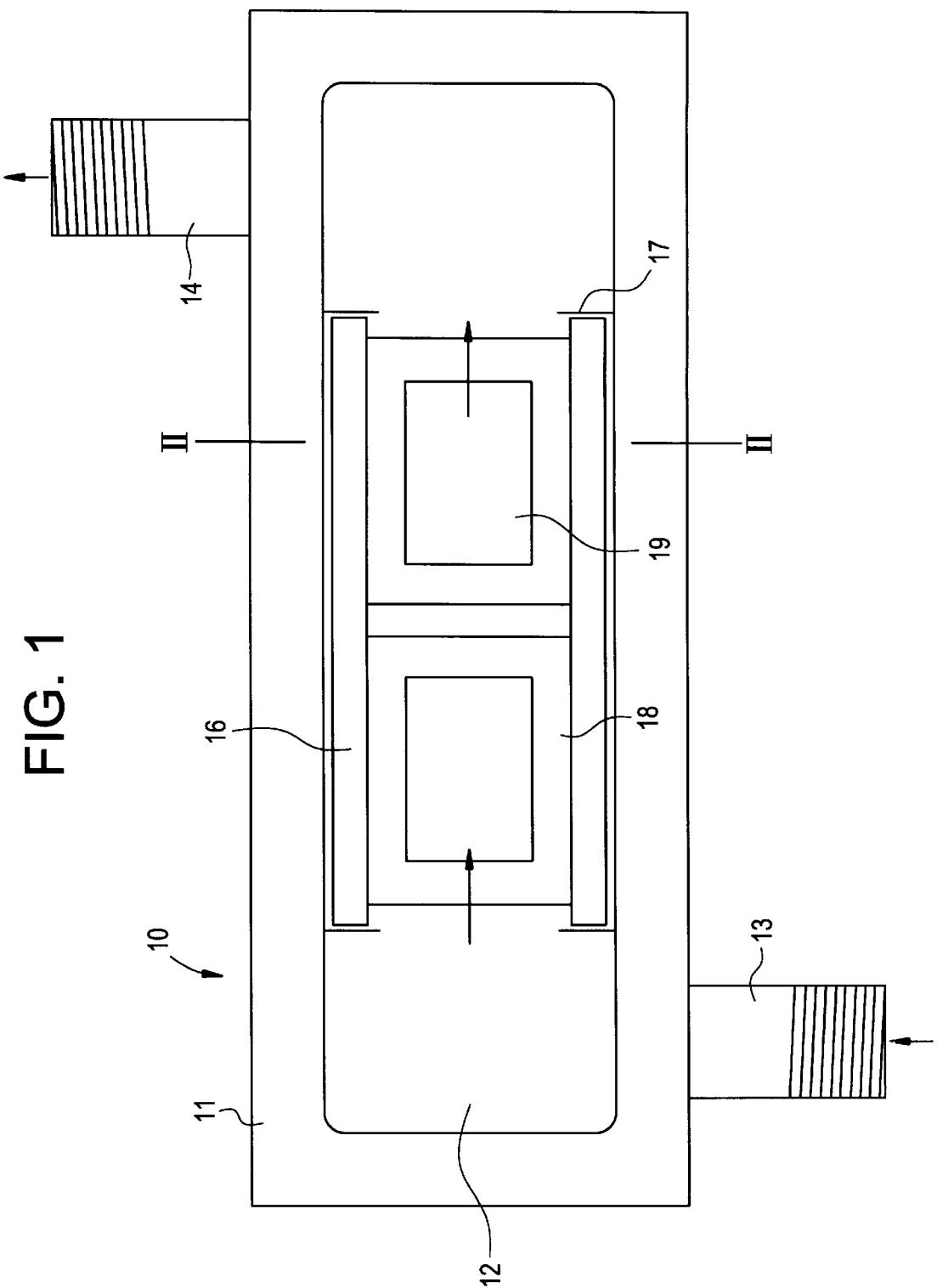
FIG. 1 illustrates a front elevational view of an apparatus for monitoring membrane deposition embodying the features of the present invention.

Turning now to the figures, where like numerals represent like parts, FIG. 1 illustrates a front elevational view of an apparatus 10 for monitoring membrane deposition made in accordance with the present invention. The apparatus 10 has an exterior body 11. The exterior body 11 can be made of any material that can withstand the temperature and pressure conditions of the specific filtration system. Under normal conditions, a water purification system can reach pressures of 180–250 psi and temperatures of 70–80° F. In extreme conditions, a pressure of 800 psi and a temperature of 120° F. can be reached in a water purification system. In a preferred embodiment, the exterior body 11 is made of a stainless steel material.

The exterior body 11 defines an interior compartment 12 for receiving a fluid stream. Preferably, the fluid stream flows through the interior compartment via at least two ports, such as ports 13 and 14. In a preferred embodiment, the direction of fluid flows into the bottom port 13 up through the top port 14.

A coupon rack 16 is positioned in the interior compartment 12. A securing means 17 is attached to the walls of the interior compartment 12 for securing the coupon holder 16 within the interior compartment 12. Like the exterior body 11, the coupon rack 16 can be made of any material that can withstand the pressure and temperature conditions of the filtration system. In an embodiment, the coupon rack 16 is made of polyvinylchloride.

At least one coupon holder 18 is suspended in the coupon rack 16. The coupon holder 18 holds at least one membrane 19. The membrane 19 collects deposition that is present within the filtration system. Since the apparatus 10 is intended to simulate a membrane element used in the filtration system, the membrane 19 is made of the same material as the membrane used in the membrane element.

For example, a common membrane used in a reverse osmosis system is a thin-layer composite. The thin-layer composite consists of a polyamide layer, a polysulfone layer, and a non-woven support. Accordingly, pursuant to the present invention, a membrane 19 used in apparatus 10 within such a reverse osmosis system would also consist of a similar thin-layer composite. Likewise, when a cellulose acetate membrane is used in the reverse osmosis system, the coupon 19 will consist of a cellose acetate membrane. However, unlike the spiral wound membranes often used in the reverse osmosis membrane element, the membrane 19 is not a coiled membrane but is preferably a single layer.

Figure 2:
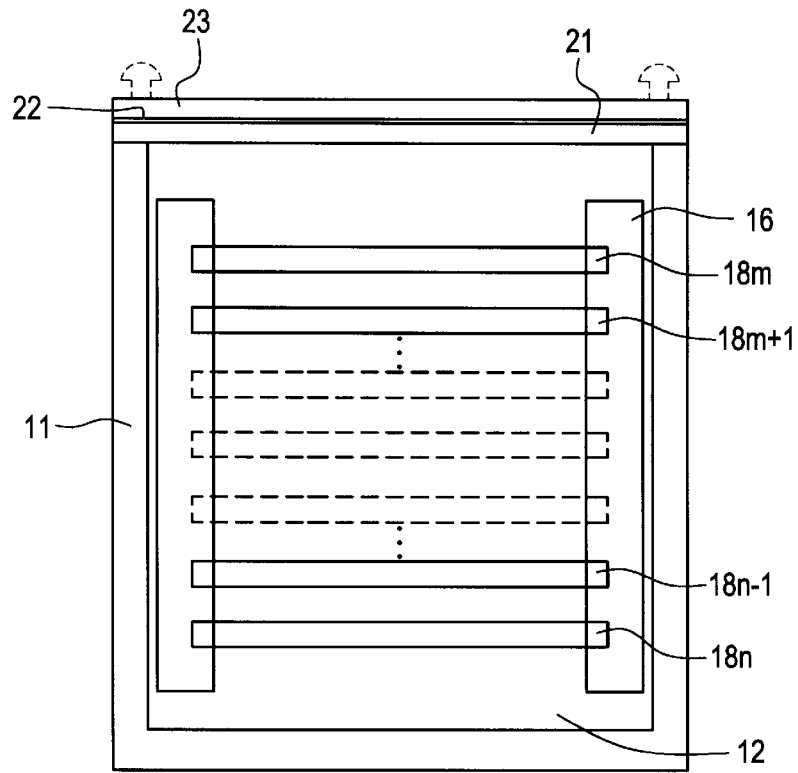
FIG. 2 illustrates a cross sectional view of a plurality of coupon holders taken generally along the line II—II of FIG. 1.

FIG. 2 illustrates a side elevational view of a coupon rack 16 suspending a plurality of coupon holders 18$m$, 18$m$+1 . . . 18$n$-1, 18$n$. The coupon rack 16 preferably has a built-in support means for suspending coupon holders 18$m$, 18$m$+1 . . . 18$n$-1, 18$n$ within the interior compartment 12.

The exterior body 11 may also include a window 21 for observation of the film formation during the filtration process. The window 21 is preferably made of a polymeric transparent material capable of withstanding the temperature and pressure of the system. A seal 22 coupled with a plate 23 can be used to properly secure the window 21 to the exterior body 11. Preferably, the plate 23 is made of the same material as the exterior body 11.

Figure 3:
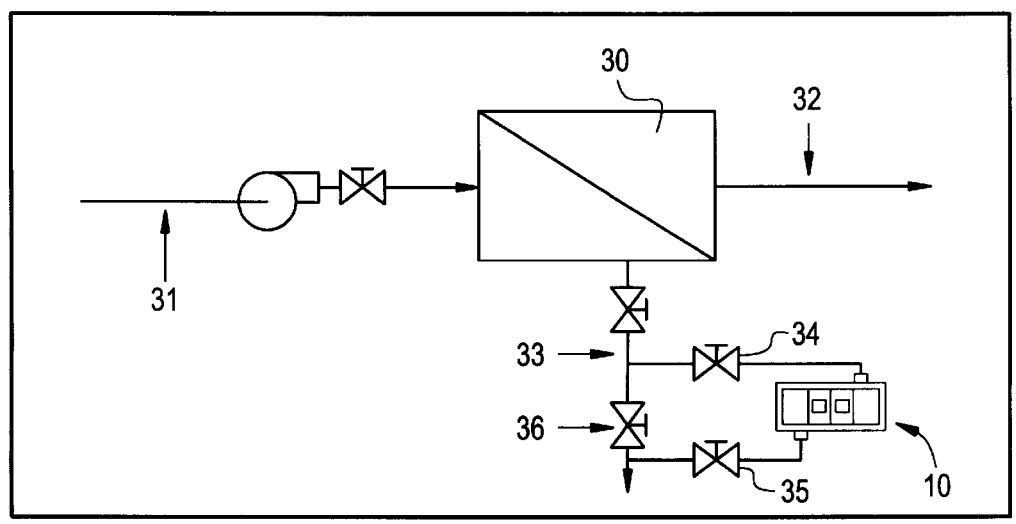
FIG. 3 illustrates the use of an apparatus of the present invention within a filtration system.

FIG. 3 illustrates generally the use of an in-line apparatus 10 for monitoring membrane deposition within a filtration system. The partial filtration system illustrated in FIG. 3 has a membrane element 30. The membrane element 30 consists of the individual components that house a membrane used within the filtration system. In an embodiment, the membrane element 30 houses a reverse osmosis membrane.

In use, a feed stream 31 is passed through the membrane element 30. The membrane element 30 acts in conjunction with the exerted pressure within the filtration system to separate the fluid stream 31 into a permeate stream 32 and concentrate stream 33. In order to monitor membrane deposition, the concentrate stream 33 is then passed through an apparatus 10 made in accordance with the present invention.

As illustrated in FIG. 3, the apparatus 10 is placed in-line with the filtration system. The amount of time the concentrate stream 33 is allowed to pass through the apparatus 10 depends on the particular system. Preferably, the concentrate stream 33 is passed through the apparatus 10 for a period ranging from 2 days to 2 months.

After a sufficient period of time has passed, valve 36 is opened and valves 34 and 35 can be closed to allow for the opening of the apparatus 10. After the exterior body 11 is opened, the technician can remove the entire coupon rack 16 from the interior compartment 12 of the apparatus 10. Then, the individual coupon holders 18 can be removed from the coupon rack 16 for subsequent analysis. In a preferred embodiment, the individual coupon holder 18 is opened and the membrane 19 is stained prior to conducting standard tests on the membrane 19. The staining of the membrane 19 is conducted with known compounds and pursuant to known methods.

An advantage of the present invention is that it allows examination of membrane deposition without sacrificing a membrane element. Rather, with the present invention, only individual membranes 19 are sacrificed to determine if any membrane deposition is occurring during the filtration process.

Moreover, the present invention avoids down time of the system and allows more frequent testing. During the removal of the membrane 19, valve 36 is opened and valves 34 and 35 are closed, resulting in no down time of the filtration system. Further, since an entire membrane element does not have to be destroyed in order to analyze for membrane deposition, the present invention allows more frequent testing.

Another advantage of the present invention is that it can be used to compare the utility of various treatments within the filtration system. For example, after analysis of the individual membranes 19, a technician is able to accurately identify the source of the problem within the filtration system. Equipped with this information, the technician can send an appropriate cleaner through the system to remedy the source problem. Or, the technician can utilize a mechanical treatment means, such as a ultraviolet source, to remedy the problem. The technician can then evaluate whether the particular treatment means is adequately treating the identified problem by testing additional membranes after the use of the treatment means.

Unlike prior monitoring programs, the apparatus 10 of the present invention allows for the accurate and early detection of membrane fouling or scaling without decreasing the recovery of the filtration system. The decrease in down time of the filtration system as well as lower replacement membrane cost can potentially result in the savings of thousands of dollars.

Figure 4:
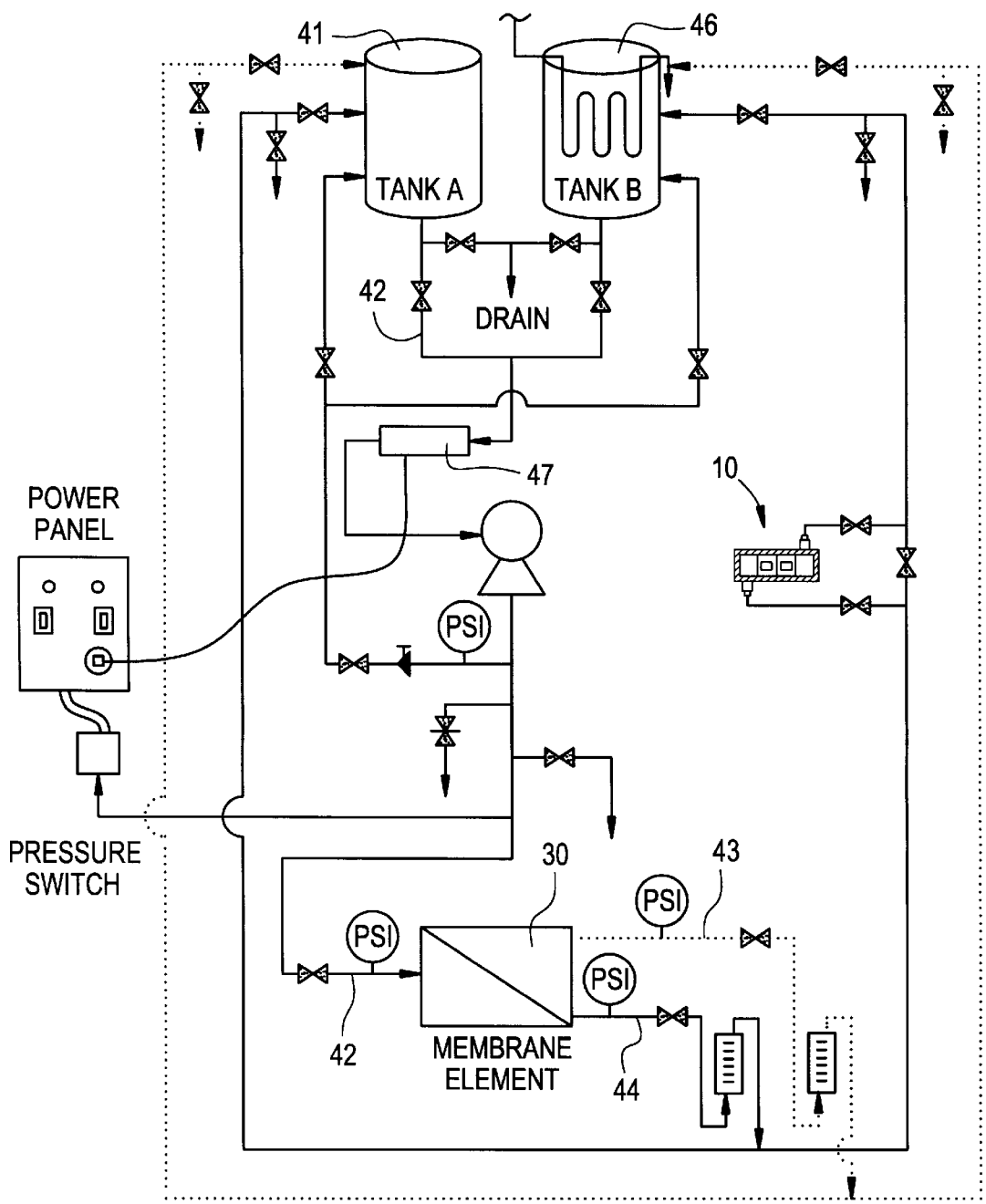
FIG. 4 illustrates a full scale filtration system incorporating the apparatus of the present invention.

FIG. 4 illustrates a full-scale filtration system incorporating an in-line apparatus 10 for monitoring membrane deposition. The filtration system of the present invention includes a feed tank 41 for depositing a fluid stream 42 into the filtration system. A membrane element 30 then receives the fluid stream 42 from the feed tank 41 and separates the fluid stream 42 into a permeate stream 43 and concentrate stream 44. In an embodiment, the membrane element 30 houses a reverse osmosis membrane. In the illustrated embodiment, the concentrate stream 44 is then passed through an apparatus 10 made in accordance with the present invention. Lastly, a storage tank 46 receives the permeate stream 43.

A filtration system utilizing the apparatus 10 of the present invention may also include a mechanical treatment means 47. In the illustrated embodiment, the mechanical treatment means 47 is an ultraviolet source. The ultraviolet rays in the ultraviolet source 47 sterilize the fluid stream 42.

The filtration system of the present invention can be used in the following manner. First, the feed tank 41 is filled with a fluid material to be filtered. Next, the fluid stream 42 is passed through a membrane element 30. The membrane element 30 separates the fluid stream 42 into a permeate stream 43 and a concentrate stream 44. The fluid stream 42 is then passed through the apparatus 10 for monitoring membrane deposition. Lastly, the permeate stream 44 is collected in a storage tank 46.

In the illustrated embodiment, the concentrate stream 44 is passed through the apparatus 10 of the present invention.

Preferably, the concentrate stream 44 is passed through the apparatus 10 as opposed to the fluid stream 42 because the concentrate stream 44 possesses a greater concentration of contaminants. Thus, passing the concentrate stream 44 through the apparatus 10 of the present invention facilitates an earlier detection of any possible membrane deposition.

Understandably, various changes and modifications to the presently preferred embodiments described herein will be apparent to those skilled in the art. Such changes and modifications can be made without departing from the spirit and scope of the present invention and without diminishing its intended advantages. Therefore, the appended claims are intended to cover such changes and modifications.

We claim:

1. An apparatus for monitoring membrane deposition in a reverse osmosis system comprising:
   an exterior body defining an interior compartment receiving a fluid stream; and
   a support member positioned in the interior compartment removably supporting a reverse osmosis membrane coupon parallel to the direction of fluid flow of the fluid stream through the interior compartment allowing the collection of deposition present within the fluid stream on the reverse osmosis membrane coupon.

2. The apparatus of claim 1 wherein the support member is a coupon rack.

3. The apparatus of claim 2 wherein the coupon rack has a support means for suspending a plurality of coupon holders.

4. The apparatus of claim 1 wherein the exterior body further includes a window for observation of film formation on the reverse osmosis membrane.

5. A method for monitoring reverse osmosis membrane deposition comprising the steps of:
   (a) passing a fluid stream through a device including an interior compartment receiving the fluid stream, and a support member holding a reverse osmosis membrane coupon parallel to the direction of fluid flow through the interior compartment;
   (b) allowing contaminants to deposit on the reverse osmosis membrane coupon from the fluid stream;
   (c) removing the reverse osmosis membrane coupon from the exterior body; and
   (d) analyzing the reverse osmosis membrane coupon.

6. The method of claim further including the step of staining the reverse osmosis membrane coupon prior to analyzing the membrane.

7. The method of claim 5 wherein the fluid stream is a concentrate stream.

8. The method of claim 5 further including the step of recycling the concentrate stream.

9. A reverse osmosis system for circulating and monitoring a fluid stream comprising:
   (a) a feed tank;
   (b) a reverse osmosis membrane element for receiving a fluid stream from the feed tank and separating the fluid stream into a permeate stream and a concentrate stream;
   (c) Means for monitoring reverse osmosis membrane deposition having an exterior body defining an interior compartment receiving the fluid stream; a coupon rack positioned in the interior compartment; and a coupon holder suspended in the coupon rack, wherein the coupon holder holds a reverse osmosis membrane parallel to the direction of fluid flow through the interior compartment, such reverse osmosis membrane collecting deposition present within the filtration system; and
   (d) a storage tank receiving the permeate stream.

10. The reverse osmosis system of claim 9 wherein the interior compartment of the means for monitoring membrane deposition receives the concentrate stream.

11. The reverse osmosis system of claim 9 further including a mechanical treatment means.

12. The reverse osmosis system of claim 11 wherein the mechanical treatment means is an ultraviolet source.

13. A method for reverse osmosis of a fluid stream including an in-line apparatus for monitoring deposition occurring on reverse osmosis membranes comprising the following steps:
   (a) filling a feed tank with the fluid stream to be treated;
   (b) passing the fluid stream through a reverse osmosis membrane element that separates the fluid stream into a permeate stream and a concentrate stream;
   (c) passing the fluid stream through an apparatus for monitoring membrane deposition having an exterior body defining an interior compartment receiving the fluid stream; a coupon rack positioned in the interior compartment; and a coupon holder suspended in the coupon rack, wherein the coupon holder holds a reverse osmosis membrane parallel to the direction of fluid flow through such interior compartment, and the reverse osmosis membrane collects deposition present within the reverse osmosis system; and
   (d) collecting the permeate stream in a storage tank.

14. The method of claim 13 wherein the interior compartment of the apparatus for monitoring deposition on the reverse osmosis membrane receives the concentrate stream.

15. The method of claim 13 further including the step of passing the fluid stream through a mechanical treatment means.

16. The method of claim 15 wherein the mechanical treatment means is an ultraviolet source.

17. The method of claim 13 further including the step of recycling the concentrate stream back into the feed tank.

* * * * *